(12) United States Patent
Bäckström et al.

(10) Patent No.: US 6,943,164 B2
(45) Date of Patent: *Sep. 13, 2005

(54) PHARMACEUTICAL SOLUTIONS OF LEVOSIMENDAN

(75) Inventors: Reijo Bäckström, Helsinki (FI); Päivi Granvik, Espoo (FI); Ritva Haikala, Espoo (FI); Sirpa Pelttari, Espoo (FI); Eva Saukko, Espoo (FI); Reija Yrjölä, Ruutana (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 10/703,565

(22) Filed: Nov. 10, 2003

(65) Prior Publication Data

US 2004/0106617 A1 Jun. 3, 2004

Related U.S. Application Data

(63) Continuation of application No. 10/070,689, filed as application No. PCT/FI00/00761 on Sep. 8, 2000, now Pat. No. 6,730,673.

(30) Foreign Application Priority Data

Sep. 10, 1999 (FI) ............................................. 19991925

(51) Int. Cl.⁷ .............................................. A61K 31/50
(52) U.S. Cl. .................................................... 514/247
(58) Field of Search ........................................ 514/247

(56) References Cited

U.S. PATENT DOCUMENTS

| 5,424,428 A | 6/1995 | Nore et al. |
| 5,512,571 A | 4/1996 | Nore et al. |
| 5,512,572 A | 4/1996 | Haikala et al. |
| 5,569,657 A | 10/1996 | Nore et al. |
| 6,180,789 B1 | 1/2001 | Timmerbacka et al. |
| 6,730,673 B1 * | 5/2004 | Backstrom et al. ......... 514/247 |

FOREIGN PATENT DOCUMENTS

| EP | 0 565 546 | 10/1993 |
| WO | WO 93/21921 | 11/1993 |
| WO | WO 97/35841 | 10/1997 |
| WO | WO 98/01111 | 1/1998 |

OTHER PUBLICATIONS

Physical Pharmacy, Martin et al. (eds.), Second Edition, published 1969 by Lea & Febiger (Philadelphia), pp 199–201.*

Sandell et al., "Pharmacokinetics of Levosimendan in Healthy Volunteers and Patients with Congestive Heart Failure," Journal of Cardiovascular Pharmacology, 26(Suppl. 1):S57–S62 (1995).

Sundberg et al., "Hemodynamic and Neurohumoral Effects of Levosimendan, a New Calcium Sensitizer, at Rest and During Exercise in Healthy Men," The American Journal of Cardiology, vol. 75, pp. 1061–1066 (1995).

Antilla et al., "Studies on Psychomotoric Effects and Pharmacokinetic Interactions of the New Calcium Sensitizing Drug Levosimendan and Ethanol," Arzneim–Forsch./Drug Res. 47 (II), Nr, 7, pp. 816–820 (1997).

Co–pending U.S. Appl. No. 10/070,689, filed, Jul. 26, 2002.

* cited by examiner

*Primary Examiner*—Raymond J. Henley, III
(74) *Attorney, Agent, or Firm*—Finnegan, Henderson, Farabow, Garrett & Dunner, LLP

(57) ABSTRACT

Levosimendan solutions for pharmaceutical use, and particularly for intravenous administration. The solutions of the invention have enhanced stability and they are particularly useful as infusion or injection solutions or infusion concentrates. Levosimendan is useful in the treatment of congestive heart failure.

5 Claims, No Drawings

PHARMACEUTICAL SOLUTIONS OF LEVOSIMENDAN

This is a continuation of application Ser. No. 10/070,689, filed on Jul. 26, 2002, now U.S. Pat. No. 6,730,673, the contents of which are incorporated by reference herein, which is a national stage filing of international application No. PCT/FI00/00761, filed on Sep. 8, 2000, which claims the benefit of priority to Finnish Patent application NO. 19991925, filed on Sep. 10, 1999.

TECHNICAL FIELD

The present invention relates to levosimendan solutions for pharmaceutical use, and particularly for intravenous administration. The solutions of the invention have enhanced stability and they are particularly useful as infusion or injection solutions or infusion concentrates. Levosimendan, or (−)-[[4-(1,4,5,6-tetrahydro-4- methyl-6-oxo-3-pyridazinyl)phenyl]hydrazono]propanedinitrile, is useful in the treatment of congestive heart failure.

BACKGROUND OF THE INVENTION

Levosimendan, which is the (−)-enantiomer of [[4-(1,4, 5,6-tetrahydro-4-methyl-6-oxo-3-pyridazinyl) phenyl] hydrazono]propanedinitrile, and methods for its preparation are described in EP 565546 B1 and WO 97/35841. Levosimendan is potent in the treatment of heart failure and has significant calcium dependent binding to troponin. Levosimendan is represented by the formula:

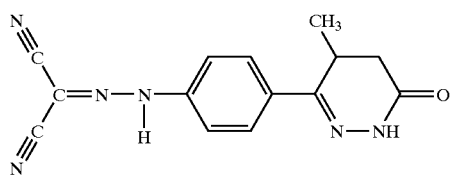

I

The hemodynamic effects of levosimendan in man are described in Sundberg, S. et al., Am. J. Cardiol., 1995; 75: 1061 –1066. Pharmacokinetics of levosimendan in man after i.v. and oral dosing is described in Sandell, E.-P. et al., J. Cardiovasc. Pharmacol., 26(Suppl.1), S57-S62, 1995. The use of levosimendan in the treatment of myocardial ischemia is described in WO 93/21921. Transdermal compositions of levosimendan are described in WO 98/01111. Clinical studies have confirmed the beneficial effects of levosimendan in heart failure patients.

Administration of a drug by parenteral, e.g. intravenous, administration provides a number of advantages including the following:

an almost immediate response may be obtained by administering by intravenous injection or infusion a solution, usually aqueous, of the drug;

the therapeutic response may be more readily controlled by administering the drug parenterally; and a drug can be administered parenterally to a patient when it cannot be administered orally because of the unconscious state of the patient, or because of inactivation or lack of absorption in the intestinal tract.

The manufacture of levosimendan solutions, and particularly solutions suitable for intravenous use, involves a number of problems which are caused by the sensitivity of levosimendan against chemical and physical influences. In solutions levosimendan is sensitive to chemical degradation which limits the shelf-life of solutions and may produce undesirable degradation products. Levosimendan is also poorly soluble in water and precipitates easily from aqueous solutions. The precipitation of intravenous solutions is extremely dangerous because particulate material may occlude the blood vessels. The solubility of levosimendan decreases further strongly when the pH is lowered from neutral, so that low pH would in principle seem unfavourable. Thus, there is a need for improved aqueous formulations of levosimendan which are chemically and physically stable under prolonged storage and suitable for intravenous administration.

SUMMARY OF INVENTION

It has now been found that the chemical stability of levosimendan solutions can be significantly improved if the pH of the solution is lowered from neutral to lower than 5, preferably to 4.5 or lower, most preferably to 3 –4.2. Furthermore, it has been found that the precipitation of the active ingredient can be prevented in such chemically stable solutions.

Thus, in one aspect, the present invention provides a pharmaceutical aqueous solution with improved stability comprising
(a) levosimendan or a pharmaceutically acceptable salt thereof as an active ingredient, the pH-value of the solution being lower than 5, preferably about 4.5 or lower, most preferably from about 3 to about 4.2, and optionally
(b) a solubility enhancing agent.

In another aspect, the invention provides an aqueous intravenous infusion solution with improved stability comprising
(a) levosimendan or a pharmaceutically acceptable salt thereof as an active ingredient, the pH-value of the solution being lower than 5, preferably about 4.5 or lower, most preferably from about 3 to about 4.2; and optionally
(b) a solubility enhancing agent.

Still in another aspect the invention provides an intravenous infusion concentrate, particularly to be diluted with an aqueous vehicle before use, comprising
(a) levosimendan or a pharmaceutically acceptable salt thereof as an active ingredient;
(b) organic solvent comprising ethanol;
(c) a stability enhancing amount of a pharmaceutically acceptable organic acid having pKa in the range of from 2 to 4; and optionally
(d) a solubility enhancing agent.

DETAILED DESCRIPTION OF THE INVENTION

Levosimendan is crystalline powder at room temperature and has pKa of 6.26. At room temperature the solubility of levosimendan in phosphate buffer is 0.4 mg/ml (pH 7.4), 0.03 mg/ml (pH 6) and 0.02 mg/ml (pH 2). Thus, the water solubility of levosimendan decreases quite sharply when pH is lowered below neutral. However, it has been found that it is possible to prepare pharmaceutically acceptable aqueous solutions of levosimendan with pH lower than 5. Such solutions are chemically and physically stable over an extended period of time and, therefore, they are particularly suitable for pharmaceutical use.

In one aspect, the invention provides a pharmaceutical composition which comprises levosimendan or a pharmaceutically acceptable salt thereof as an active ingredient in an aqueous solution with pH lower than 5, preferably about 4.5 or lower, and most preferably from about 3 to about 4.2. The composition of the invention is particularly useful in various pharmaceutical applications in which levosimendan must be stored in the form of an aqueous solution for an extended period of time.

The therapeutically effective amount of levosimendan included in the composition of the invention depends e.g. on the administration route of the composition, the treatment procedure and the condition to be treated. In general, the amount of levosimendan in the composition is within the range of about 0.001 –5 mg/ml. The daily dosage of levosimendan in man is within the range of about 0.1 –50 mg, preferably about 0.2–20 mg, depending on the administration route, age, body weight and condition of the patient. Preferred peak plasma levels of levosimendan in steady state for the treatment of congestive heart failure are within the range of from about 1 to about 300 ng/ml, more preferably from about 10 to about 150 ng/ml, and especially from about 20 to about 60 ng/ml. Levosimendan can be administered intravenously with the infusion rate in the range of about 0.005–100 µg/kg/min, typically 0.01 to 10 µg/kg/min, more typically about 0.02 to 1 µg/kg/min. For the treatment of heart failure, with continuous infusion the suitable rate is 0.05–0.4 µg/kg/min of levosimendan.

Salts of levosimendan may be prepared by known methods. Pharmaceutically acceptable salts are useful as active medicaments, however, preferred salts are the salts with alkali or alkaline earth metals.

The control of pH of the composition is essential to maintain the required stability of the active ingredient. Therefore, a suitable pharmaceutically acceptable acidic compound or buffer system in an amount effective to maintain the pH of the composition in the desired range, may be used. Preferred acidic compounds include pharmaceutically acceptable organic acids having pKa in the range of from about 2 to about 4. Such acids include 2-hydroxy alkanoic acids, such as citric acid, lactic acid, tartaric acid or malic acid. If a pharmaceutically acceptable buffer system is used, it is selected from a group of buffers that are effective to maintain pH below 5, preferably at 4.5 or lower, most preferably in the range of about 3–4.2, which buffers are well known in the art. Most preferably the buffer may be selected from citrate, acetate, phosphate and lactate buffers. The preparation of buffer systems is well known for one skilled in the art. In general, the acidic compound or buffer is used in an amount necessary to adjust the pH into the desired range. However, the amount used must be pharmaceutically acceptable.

The composition of the invention may also comprise a solubility enhancing agent. The term "solubility enchancing agent" means herein a substance capable of increasing the amount of levosimendan that can be maintained in a dissolved state in an aqueous solution, including the prevention of crystallization or crystalline growth of levosimendan. Suitable solubility enhancing agents include co-solvents such as ethanol or propylene glycol, surfactants and polymeric substances such as polysorbates, polyalkylene glycols (e.g. polyethylene glycol), poloxamers or polyvinylpyrrolidone, and oily fatty acids and their mono- or diglyceryl esters such as linoleic acid or glyceryl monolaurate. In general, the amount of the solubility enhancing agent is within the range of about 0.001–80%, preferably 0.005–10%, most preferably 0.01–5%, by weight of the composition. For intravenous administration, wherein the choice of acceptable adjuvants is limited, polyvinylpyrrolidone or ethanol or a mixture thereof is the preferred solubility enhancing agent polyvinylpyrrolidone being the most preferred. Suitable polyvinyl pyrrolidones are those with a number average weight below 40,000, more suitably below 5000, and particularly about 2,500. Such a polyvinyl pyrrolidone is exemplified by Kollidon PF12 (registered trademark).

It will be understood that various additives commonly used in this field of the art, such as preservatives, can be also included in the composition of the invention.

In another aspect, the invention provides an aqueous intravenous solution comprising levosimendan or a salt thereof as an active ingredient the pH-value of the solution being lower than 5, preferably about 4.5 or lower, and most preferably from about 3 to about 4.2. The aqueous intravenous solution, which can be in a form of e.g. an injection or infusion solution, of the invention is chemically and physically stable under storage conditions over an extended period of time. Preferably the aqueous intravenous solution is a ready to use intravenous solution for infusion or bolus injection.

The amount of levosimendan included in the aqueous intravenous solution of the invention depends e.g. on the treatment procedure and the condition to be treated, but is generally a therapeutically effective amount. The amount may vary e.g. within the range of about 0.001–1.0 mg/ml, preferably about 0.005–0.5 mg/ml, most preferably about 0.01–0.1 mg/ml.

For maintaining the pH of the aqueous intravenous composition of the invention in the desired range a suitable pharmaceutically acceptable acidic compound or buffer system may be used as described above.

The aqueous intravenous composition of the invention may also comprise a solubility enhancing agent for increasing the amount of levosimendan that can be maintained in a dissolved state in an aqueous solution, including the prevention of crystallization or crystalline growth of levosimendan. For intravenous administration, wherein the choice of acceptable adjuvants is limited, polyvinylpyrrolidone or ethanol or a mixture thereof is the preferred solubility enhancing agent polyvinylpyrrolidone being the most preferred. The amount of the solubility enhancing agent in the aqueous intravenous composition is generally within the range of about 0.001–20%, preferably 0.005–5%, by weight of the aqueous intravenous composition. The preferred amount of polyvinylpyrrolidone is within the range of about 0.005–0.5% by weight of the aqueous intravenous composition.

The aqueous intravenous composition of the invention may also comprise a physiologically and pharmaceutically acceptable compound effective to render the aqueous intravenous composition isotonic, i.e. to have an osmotic pressure corresponding to that of a 0.9% solution of sodium chloride. Typical examples of such compounds are chloride salts such as NaCl and saccharides such as sorbitol, mannitol and dextrose/glucose. The preparation of isotonic solutions is well known for one skilled in the art.

The aqueous intravenous composition of the invention may be prepared e.g. by dissolving levosimendan and other adjuvants into sterile isotonic aqueous vehicles, e.g. 0.9% solution of sodium chloride while,stirring. Alternatively a suitable amount of isotonic rendering compound is dissolved together with levosimendan and other adjuvants into aqueous vehicle, e.g. sterile distilled water. The solution may be also prepared by dissolving levosimendan and other adjuvants first in suitable solvent such as ethanol, and diluting the solution with sterile isotonic aqueous vehicles. The bulk solution is filtered and filled into infusion bottles or ampules. The product is sterilized preferably using autoclaving in a manner known in the art.

In yet another aspect the invention provides a pharmaceutical solution, particularly an intravenous infusion concentrate to be diluted with an aqueous vehicle before use, comprising (a) levosimendan or a pharmaceutically acceptable salt thereof as an active ingredient, (b) pharmaceutically acceptable organic solvent comprising ethanol, preferably dehydrated ethanol, and (c) a stability enhancing amount of a pharmaceutically acceptable organic acid having pKa in the range of from about 2 to about 4. It has been found that the pharmaceutically acceptable organic acid having pKa in the range of from about 2 to about 4 improves the stability of levosimendan in the concentrate solutions of the invention. It has also been found that the concentrate solutions of the invention can be successfully diluted with an aqueous infusion vehicle to obtain aqueous intravenous solutions which are chemically and physically stable over an extended period of time.

The amount of pharmaceutically acceptable organic solvent is generally within the range of 90–99.9%, preferably 95–99.9%, by weight of the concentrate solution of the invention. Typically at least about 50% by weight of the solvent is ethanol. More suitably, the solvent consists essentially of ethanol, whereby at least 90%, preferably at least 95%, more preferably at least 99%, by weight of the solvent is ethanol. Most preferably the solvent consists solely of ethanol, preferably dehydrated ethanol.

The amount of said pharmaceutically acceptable organic acid is preferably within the range of 0.005–2%, preferably 0.01–1%, by weight of the concentrate solution. Said pharmaceutically acceptable organic acid is a preferably a 2-hydroxy alkanoic acid. Such acids, include citric acid, lactic acid, tartaric acid and malic acid the most preferred being citric acid.

The amount of levosimendan included in the concentrate solution of the invention is generally an amount which is therapeutically effective. The amount may vary e.g. within the range of about 0.1–10 mg/ml, preferably about 0.5–8 mg/ml, most preferably about 1–5 mg/ml.

The concentrate solution of the invention may also comprise a solubility enhancing agent for increasing the amount of levosimendan that can be maintained in a dissolved state in an aqueous solution, including the prevention of crystallization or crystalline growth of levosimendan. The amount of the solubility enhancing agent in the concentrate solution of the invention is generally within the range of about 0.01–5%, by weight of the composition. The solubility enhancing agent can be selected as described above. The most preferred solubility enhancing agent is polyvinylpyrrolidone. The preferred amount of polyvinylpyrrolidone is generally within the range of about 0.5–2%, by weight of the concentrate composition.

A particularly preferred concentrate solution for intravenous infusion comprises (a) levosimendan or a pharmaceutically acceptable salt thereof in amount of 0.01–1.0% by weight, (b) dehydrated ethanol in amount of 95–99.5% by weight, (c) citric acid in amount of 0.03–0.6% by weight, and (d) polyvinylpyrrolidone in amount of 0.5–2% by weight.

The concentrate solution may be prepared by dissolving stability enhancing organic acid, levosimendan and the optional solubility enhancing agent and possible other additives to the solvent in the sterilized preparation vessel under stirring. The resulting bulk solution is filtered through a sterile filter. The sterilization method of the product is preferably a sterile filtration, because ethanol solution cannot be autoclaved due to the explosion risk. The sterile filtered bulk solution is aseptically filled into injection vials and closed with rubber closures.

The concentrate solution for intravenous infusion is diluted with an aqueous vehicle before use. Typically the concentrate solution is diluted with aqueous isotonic vehicles for intravenous infusion, such as 5% glucose solution or 0.9% NaCl solution. The concentrate infusion is diluted such that an aqueous intravenous solution is obtained, wherein the amount of levosimendan is generally within the range of about 0.001–1.0 mg/ml, preferably about 0.005–0.5 mg/ml, most preferably about 0.01–0.1 mg/ml, depending e.g. on the treatment procedure and the condition to be treated.

The invention is illustrated but in no way limited, by the following examples.

EXAMPLE

Concentrate Solution for Intravenous Infusion

| | |
|---|---|
| (a) levosimendan | 2.5 mg/ml |
| (b) Kollidon PF12 | 10 mg/ml |
| (c) citric acid | 2 mg/ml |
| (d) dehydrated ethanol | ad 1 ml (785 mg) |

The concentrate solution was prepared by dissolving citric acid, Kollidon PF121 and levosimendan to dehydrated ethanol in the sterilized preparation vessel under stirring. The resulting bulk solution was filtered through a sterile filter (0.22 $\mu$m). The sterilization method of the product was sterile filtration, because ethanol solution cannot be autoclaved due to the explosion risk. The sterile filtered bulk solution was then aseptically filled into 8 ml and 10 ml injection vials (with 5 ml and 10 ml filling volumes) and closed with rubber closures. The product has a shelf-life of 2 years in 2 –8° C.

EXAMPLE 2

The effect of citric acid on the chemical stability of levosimendan in ethanolic infusion concentrate solutions stored in different temperatures was studied. The solutions were prepared as described in Example 1. The results are shown in Tables 1 and 2. In the Tables "OR-1746" refers to (4-Ethoxy-6-imino-5 {[4(4-methyl-6-oxo-1,4,5,6-tetrahydro-pyridazin-3-yl)-phenyl]hydrazono}-5,6-dihydro-1(H)-pyrimidin-2-ylidene)-[4-(4-methyl-6-oxo-1,4,5,6-tetrahydro-pyridazin-3-yl)-phenylazo]acetonitrile.

TABLE 1

Effect of citric acid on the chemical stability of levosimendan. All solutions contain levosimendan (1.25 mg/ml), Kollidon PF12 (10 mg/ml) and dehydrated ethanol (ad 1 ml).

| Citric acid | Storage time/Amount of degradation product (OR-1746) | |
|---|---|---|
| mg/ml | 2–8° C. | 40° C. |
| 0 | 5 weeks/0.34% | 5 weeks/10.9% |
| 0.25 | 13 weeks/0.29% | 13 weeks/6.2% |
| 0.50 | 13 weeks/0.20% | 13 weeks/4.4% |

TABLE 1-continued

Effect of citric acid on the chemical stability of levosimendan.
All solutions contain levosimendan (1.25 mg/ml), Kollidon PF12
(10 mg/ml) and dehydrated ethanol (ad 1 ml).

| Citric acid | Storage time/Amount of degradation product (OR-1746) | |
|---|---|---|
| mg/ml | 2–8° C. | 40° C. |
| 0.75 | 13 weeks/0.16% | 13 weeks/3.5% |
| 1.00 | 13 weeks/0.13% | 13 weeks/3.0% |
| 1.50 | 13 weeks/0.10% | 13 weeks/2.2% |
| 2.00 | 13 weeks/0.10% | 13 weeks/1.7% |

TABLE 2

Effect of citric acid on the chemical stability of levosimendan.
All solutions contain levosimendan (2.50 mg/ml), Kollidon PF12
(10 mg/ml) and dehydrated ethanol (ad 1 ml).

| Citric acid | Storage time/Amount of degradation product (OR-1746) | |
|---|---|---|
| mg/ml | 2–8° C. | 40° C. |
| 0 | 12 months/3.94% | nd |
| 2.0 | 4 months/0.20% | 4 months/5.6% |
| | 12 months/0.39% | nd |
| | 18 months/0.59% | nd |
| 2.5 | 4 months/0.16% | 4 months/3.2% |
| | 12 months/0.28% | nd |
| | 18 months/0.47% | nd | nd = not determined

The results show that citric acid significantly improves the chemical stability of levosimendan in infusion concentrate solutions.

EXAMPLE 3

Aqueous Solution for Infusion, pH 3.9

| (a) levosimendan | 0.025 mg/ml |
|---|---|
| (b) Kollidon PF12 | 0.10 mg/ml |
| (c) citric acid | 0.02 mg/ml |
| (d) ethanol | 7.85 mg/ml |
| (e) sodium chloride | 9.0 mg/ml |
| (e) water | ad 1 ml |

The above aqueous infusion solution was obtained by diluting the infusion concentrate solution of Example 1 with isotonic (0.9%) sodium chloride solution such that the resulting aqueous solution contained 0.025 mg/ml of levosimendan. The diluted solution was clear with no precipitation.

The chemical stability of levosimendan in the aqueous solution of Example 3 was studied after 24 hour storage (at room temperature) and after one month storage (at 2–8° C.). The results are shown in Table 3. "OR-1420" refers to (E)-2-cyano-2 –[[4–(1,4,5,6-tetrahydro-4-methyl-6-oxo-3-pyridazinyl)phenyl]hydrazono]acetamide.

TABLE 3

The chemical stability of levosimendan in a solution of Example 3
after the storage of 24 hours (at room temperature 25° C.)
and after the storage of one month (at 2–8° C).

| | 0 h | 24 h | 1 month |
|---|---|---|---|
| Degradation product OR-1420 | < | < | 0.1% |
| Degradation product OR-1746 | 0.1% | 0.1% | < |
| Unknown degradation products | < | < | < |
| pH | 3.9 | nd | 3.9 |

< = under quantitation limit 0.1%
nd = not determined

For comparison, the chemical stability of levosimendan in Reference solutions having pH of 7–8 was studied after the storage of 2 and 5 days at 8–15° C. and room temperature. The results are shown in Table 4.

Reference Solutions:

| (a) levosimendan | 0.01–0.25 mg/ml |
|---|---|
| (b) sodium chloride | 9 mg/ml |
| (c) sodium carbonate monohydr. | 0.02–0.5 mg/ml |
| (d) hydrochloric acid 0.1 M | to adjust pH to 7–8 |
| (e) water | ad 1 ml |

TABLE 4

The chemical stability of levosimendan in Reference solutions (0.01,
0.1 and 0.25 mg/ml of levosimendan) having pH of 7–8 after the
storage of 2 and 5 days at 8–15° C. and room temperature (25° C.).

| | Levosimendan mg/ml | 0 h | 2 days 8–15° C./25° C. | 5 days 8–15° C./25° C. |
|---|---|---|---|---|
| Degradation product OR-1420 | 0.01 | < | 1.6%/3.3% | 2.2%/6.0% |
| | 0.1 | 1.5% | 1.1%/1.8% | 1.8%/5.3% |
| | 0.25 | 0.4% | 0.8%/2.2% | 1.4%/4.2% |
| Unknown degradation products | 0.01 | nd | nd | nd |
| | 0.1 | < | 0.2%/0.4% | 0.2%/0.6% |
| | 0.25 | < | 0.3%/0.5% | 0.3%/0.9% |
| pH | 0.01 | 7.2 | 7.2/7.3 | 7.3/7.3 |
| | 0.1 | 7.8 | 7.8/7.8 | 8.0/8.0 |
| | 0.25 | 7.8 | 7.8/7.8 | 8.0/8.0 |

< = under quantitation limit 0.1%
nd = not determined

The results show that degradation of levosimendan is significantly retarded in the solution of Example 3 compared to Reference solutions. In the Reference solutions significant amounts of degradation products are formed already after the storage of 5 days, whereas the solution of Example 3 is stable even after the storage of one month. It can be also noted that the pH tends to increase in Reference solutions.

What is claimed is:

1. An aqueous intravenous infusion solution comprising levosimendan or a salt thereof as an active ingredient, the pH-value of the solution being 3 or higher but lower than 5, and optionally a solubility enhancing agent.

2. solution according to claim 1, the pH-value of the solution being in the range of from 3 to about 4.2.

3. A solution according to claim 1, wherein the solubility enhancing agent is polyvinylpyrrolidone or ethanol.

4. A solution according to claim 1, wherein the pH-value of the solution is about 4.5 or lower.

5. A solution according to claim 2, wherein the solubility enhancing agent is polyvinylpyrrolidone or ethanol.

* * * * *